United States Patent [19]

Howison

[11] 4,237,813

[45] Dec. 9, 1980

[54] WARNING AND PROTECTIVE DEVICE

[76] Inventor: Ronald G. Howison, 84 Gladstone Rd., Mosgiel, New Zealand

[21] Appl. No.: 924,397

[22] Filed: Jul. 13, 1978

[30] Foreign Application Priority Data

Jul. 22, 1977 [NZ] New Zealand ............ 184718

[51] Int. Cl.³ .............................................. G01I 19/12
[52] U.S. Cl. ...................................... 116/70; 137/557
[58] Field of Search ............... 116/70; 128/142.2, 188, 128/142.4, 142.3; 137/557

[56] References Cited

U.S. PATENT DOCUMENTS

| | | | |
|---|---|---|---|
| 3,611,981 | 10/1971 | Warncke | 128/142.3 X |
| 3,785,333 | 1/1974 | Warncke | 128/142.3 X |
| 3,910,222 | 10/1975 | Metivier | 116/70 |

FOREIGN PATENT DOCUMENTS 1104829 4/1961 Fed. Rep. of Germany ........ 128/142.2

Primary Examiner—Harry N. Haroian
Attorney, Agent, or Firm—Holman & Stern

[57] ABSTRACT

A warning and protection device particularly suitable for use in gas anaesthetizing systems is provided, the device having means communicable with each of two gases used in the anaesthetizing process. The means communicable with one of the gas sources includes a pressure sensitive component which in turn is associated with a valve in the second gas means, the construction and arrangement being such that when a drop in gas pressure within the first gas means is sensed below a predetermined value the gas flow through the second gas means is blocked off.

16 Claims, 5 Drawing Figures

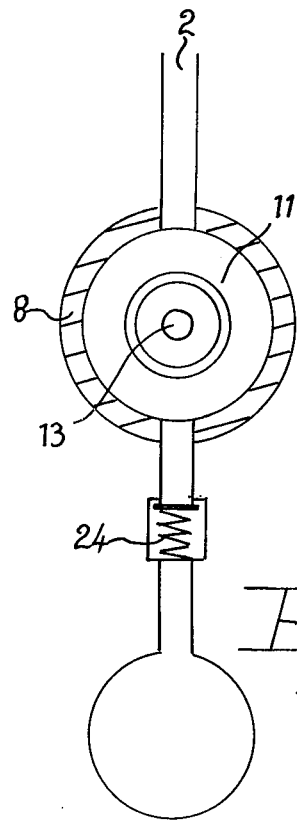
Fig. II
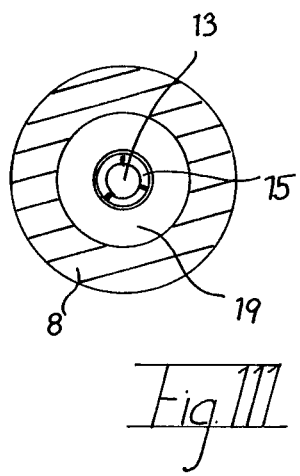
Fig. III
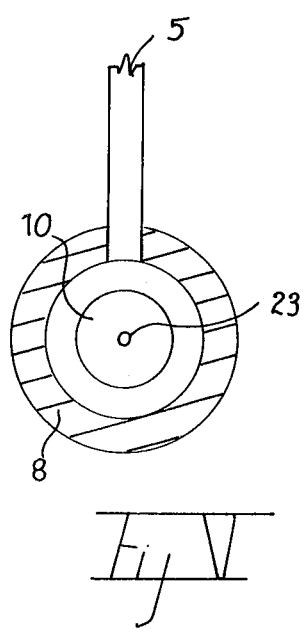
Fig. IV
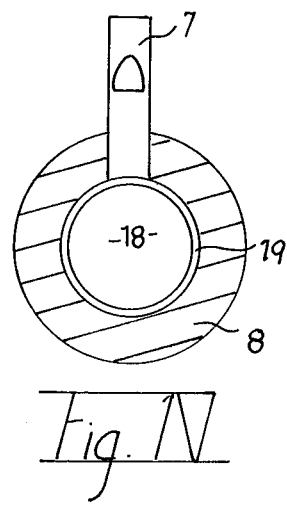
Fig. IV

WARNING AND PROTECTIVE DEVICE

FIELD OF THE INVENTION

This invention relates to a warning and protection device and in particular, although not necessarily solely, to a patient protection and warning device for use in conjunction with gas anaesthetizing systems.

BACKGROUND OF THE INVENTION

It is common medical practice to administer nitrous oxide to patients in order to anaesthetize them for surgery. Once the patient has been initially anaesthetized, they may be maintained in such a condition by the balanced administration of oxygen and nitrous oxide. If, for some reason, the oxygen supply should fail the anaesthetized patient could receive an excess dose of nitrous oxide which could, if allowed to pass undetected, prove fatal.

People within the medical profession have long realised the possibility of such an occurrence and various members of the medical profession, particularly those amongst the anaesthetists, have studied this problem and have made recommendations concerning the prevention of such an occurrence.

By way of example, the standing sub-committee on safety in anaesthesia of the Association of Anaesthetists of Great Britain and Ireland have published a guide in regard to this matter, which guide recommends inter alia:

The device should be relatively cheap. It should be easily fitted and should be capable of working satisfactorily on all the continuous or intermittent flow machines in common use, whether the oxygen supply is obtained from cylinders or from a pipe-line installation.

The device should preferably be fitted permanently to the machine. If all or part of the device has to be detachable (e.g. for sterilisation) it should be so designed that it is impossible to give an anaesthetic with that machine unless the detachable part has been correctly replaced.

The device should be mounted in an obvious position. If this is not possible a label should be permanently attached to the machine in a prominent place to indicate that the device has been fitted. The label should indicate the purpose, mode of function and method of testing the device and should be easily visible from the front of the machine.

The device should be automatically tested whenever the oxygen supply is switched on or off. Provision for testing at other times may be incorporated if desired.

The energy required to operate the device should be derived solely from the normal oxygen supply pressure in the line between the cylinder or pipe-line inlet to the machine and the oxygen flowmeter control valve.

The device should be activated when this pressure falls to a value which is ideally not less than two-thirds and certainly not less than half of the normal oxygen supply pressure to the flowmeter.

When the device is activated it should give an audible and, if desired, visible warning of the reduction in oxygen supply pressure even if the patient is not breathing.

The audible warning should have a distinctive sound, be clearly audible to a person with normal hearing above a background noise level that may be expected in an operating theatre. The Committee suggests that an 80 dB whistle would be adequate but the necessary experimental work has yet to be done. The sound should last for at least 10 seconds. These requirements should be met whether the oxygen supply pressure failure is caused by cylinder emptying or pipe-line disconnection.

It should not be possible to supply any other gas to the patient unless the oxygen supplies to the flowmeter and oxygen bypass valve are connected and are at their designed operating pressure.

It is therefore an object of the present invention to provide a safety and protection apparatus which will go at least some way in achieving the requirements hereinbefore set forth.

SUMMARY OF THE INVENTION

Accordingly, in one aspect, the invention consists in a warning and protection apparatus including:

a first gas receiving or conveying means; pressure sensitive means within said first-gas receiving or conveying means actuable in the event of a variation in pressure from a predetermined range or value in a gas stream present in said first gas receiving or conveying means; a second gas conveying means; a valve, associated with said pressure sensitive means, adapted to control or block off a gas stream within said second gas conveying means upon said variation being sensed; alarm means actuable when said variation is sensed to indicate the existence of said variation; and a first gas reserve storage means adapted to maintain said stream of gas present in said first gas receiving or conveying means for at least a portion of the time in which said variation is present.

The first gas receiving or conveying means and the second gas conveying means preferably comprise a pair of chambers attachable to respective supplies of first and second gas. A portion of each of the chamber walls is preferably defined by or includes a flexible diaphragm, the diaphragm forming part of the pressure sensitive means in the first gas chamber and part of the valve in the second gas chamber.

The diaphragm in the first gas chamber is preferably biased, on that side thereof remote from the chamber interior, by a spring under compression, the compression of the spring being set so that the diaphragm assumes a substantially planar configuration when the gas within the first gas chamber is at or within the predetermined safe operating value or range.

The alignment of each diaphragm in its respective chamber is preferably such that the two diaphragms are substantially parallel, the two diaphragms preferably being physically inter-associated such that if the diaphragm in the first gas chamber deflects due to a drop in the gas pressure within the first gas chamber, then that in turn, will lead to a deflection of the diaphragm in the second gas chamber. A pair of co-axial push rods is preferably provided to form the physical association.

An intermediate gas chamber is preferably provided in a common means defining a body member with the first and second gas chambers. The intermediate gas chamber is preferably associable both with the first gas chamber and with the first gas reserve storage means. The alarm means is preferably tapped from the intermediate gas chamber, the construction and configuration being such that when a decrease in the pressure of gas within the first gas chamber below a critical value is sensed the contents of the first gas reserve storage means are opened to the intermediate gas chamber from which they flow into the first gas chamber, a portion of the gas passing through the alarm means to activate the same.

The alarm means is preferably an audible whistle.

In a further aspect the invention consists in a patient protection and oxygen failure warning device for use in an anaesthetising system including the apparatus set forth in the preceding paragraphs wherein in use, the first gas receiving or conveying means receives or conveys oxygen and the second gas conveying means conveys nitrous oxide.

In still a further aspect the invention may broadly be said to consist in an anaesthetizing system comprising supply means to supply anaesthetizing and/or life support gases to a patient; means for providing, in use, a primary supply of life support gases to said supply means; means for providing, in use, a secondary supply of life support gases to said supply means; means for providing, in use, a supply of an anaesthetizing gas to said supply means; and control means which, in normal use, supplies or regulates only gases from said primary supply and said anaesthetizing supply to said supply means but which will, without human intervention, upon a failure wholly or in part of said primary supply, stop the anaesthetizing supply and commence the secondary supply to said supply means.

BRIEF DESCRIPTION OF THE DRAWINGS

One embodiment of the invention will now be described with reference to the accompanying drawings in which:

FIG. I depicts a schematic cross-sectional view of a warning and protection device according to the invention, FIG. II depicts a view along the line II—II in FIG. I, FIG. III depicts a view along the line III—III in FIG. I, FIG. IV depicts a view along the line IV—IV in FIG. I, and FIG. V depicts a view along the line V—V in FIG. I.

DESCRIPTION OF THE PREFERRED EMBODIMENT

Figure 1:
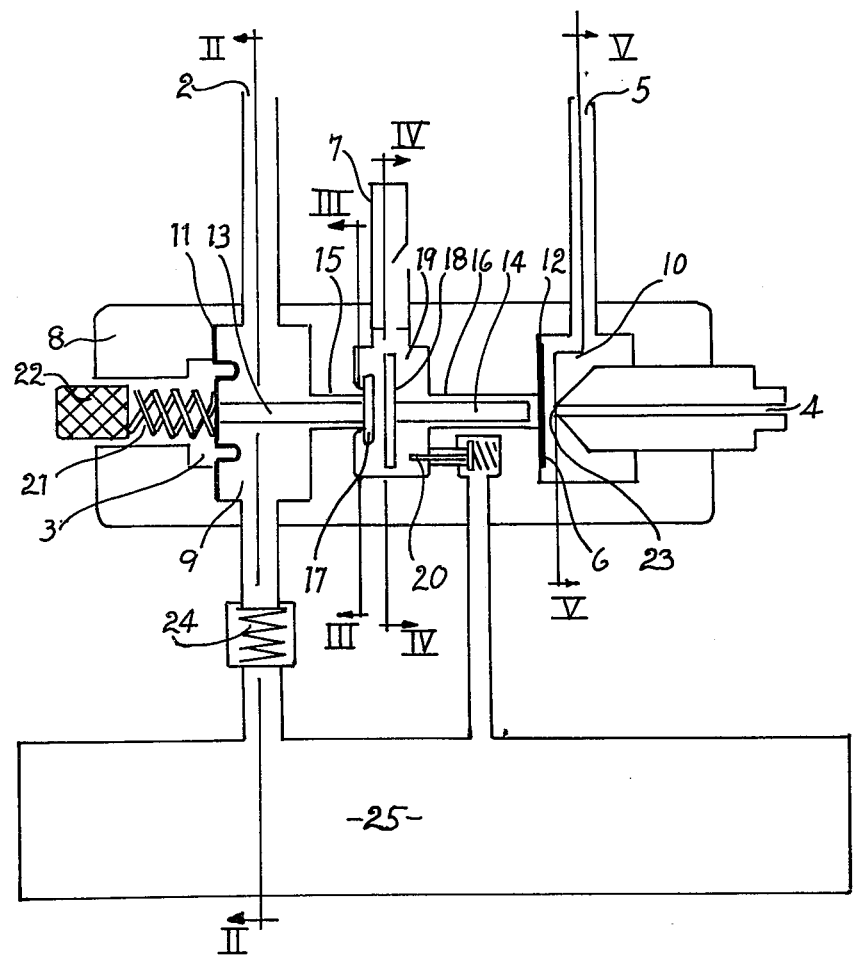

In accordance with the invention there is provided a warning and protection apparatus having a first gas receiving means, including a first gas inlet 2 and a pressure sensitive means, generally designated 3 within said first gas receiving means, the pressure sensitive means being adapted to sense a variation in pressure in a stream of gas associated with the first gas receiving or conveying means. In this embodiment, the first gas receiving or conveying means is tapped, through a T-connector or the like (not shown) from a first gas supply line (not shown). The apparatus further includes a second gas conveying means having inlet at 4 and an outlet at 5. Situated between the inlet 4 and the outlet 5 of the second gas conveying means is a valve generally designated 6, which valve is associated with the pressure sensitive means 3 and is adapted to control or block off a stream of gas passing through the second gas conveying means when a variation in pressure outside the acceptable value or range is sensed by the sensitive means 3. As described above in this embodiment the first gas inlet 2 is tapped off a first gas stream but a similar apparatus might be produced having the first gas stream passing therethrough without departing from the scope of this invention.

In accordance with its function as a warning device, the apparatus further includes an alarm means 7 which is actuated upon the aforementioned variation being sensed and in keeping with its function as a protection device, a first gas reserve storage tank generally designated 25 is provided, which reserve storage tank is adapted to maintain a stream of gas in the first gas supply stream for at least a portion of the time during which the aforementioned variation is present in the system.

The first gas receiving or conveying means and the second gas conveying means each comprise cylindrical chambers indicated by numerals 9 and 10 respectively.

Part of the wall area of each of the chambers 9 and 10, is defined by, or includes a diaphragm, the diaphragms being numbered in the FIGS. 11 and 12 respectively. The diaphragm 11 in combination with coil spring 21 constitutes the pressure sensitive means while the diaphragm 12, in a manner hereinafter described, constitutes the valve 6 operable to block off the flow of second gas. As can be seen from the figure, diaphragms 11 and 12 are mounted on or constitute, one flat, end wall of their respective chambers 9 and 10 in a parallel manner and are physically associated with one another through push-rods 13 and 14 which are mounted co-axially between the first and second gas chambers. As can be seen from the figure, push-rod 13 is supported in bore 15 and push-rod 14 is supported in bore 16. The adjacent ends of push-rods 13 and 14 are provided with striker plates 17 and 18 respectively, the striker plates being formed in planes perpendicular to the axis of the push-rods.

Formed between the first gas chamber 9 and the second gas chamber 10 is an intermediate chamber 19 which is isolated from the second gas chamber 10 but is communicable with the first gas chamber 9 through a port surrounding bore 15. As can be seen from the figure, the striker plates 17 and 18 lie within the similarly cylindrical intermediate chamber 19. The intermediate chamber 19 is in further isolatable communication with the first gas reserve storage means 25 (through valve 20) and also serves to provide an actuating source for the alarm means 7.

The second gas inlet feeds through an orifice 23 whose axis is arranged substantially perpendicular to the plane of the second gas diaphragm 12, the orifice 23 and the diaphragm 12 constituting the valve designated with the numeral 6 hereinabove.

The first and second gas chambers and the intermediate chambers are all formed within a common means 8 defining a body member, which body member also locates and retains diaphragms 11 and 12, push rods 13 and 14, spring 21 with associated adjuster 22, alarm 7 and valve 20.

The operation of the apparatus is as follows: with the first gas supply initially disconnected the diaphragm 11 is displaced to the right as shown in the drawing by the coil spring 21 expanding. The diaphragm 11 in turn displaces push-rod 13 to the right which in turn contacts and displaces push-rod 16 accordingly. Push-rod 16 in turn contacts diaphragm 12 which is displaced to the right until it contacts and seals on orifice 23 thus preventing a flow of gas from passing through the second gas inlet 4.

On a supply of gas being established in the first gas supply line, a portion of the first gas flows through inlet 2 (the first gas receiving means) into the first gas chamber 9 and into reserve gas reservoir 25 via non-return valve 24. At the same time a small amount passes into the intermediate chamber 14 via the port about bore 15 and out through the alarm whistle 7 activating the same to give a test indication that the apparatus is in working order.

As the pressure of the gas supply stream builds up so does the pressure of gas build up within the reserve storage tank, until when the desired, predetermined safe operating pressure of the first gas stream is reached the non-return valve 24 closes (thus trapping a supply of the gas in the reservoir 25 at the desired delivery pressure) and, since the pressure within chamber 9 is at the predetermined supply pressure of the first gas stream, the diaphragm 11 is displaced, against the bias of spring 24, to the substantially planar form shown in FIG. I. As the diaphragm 11 assumes the planar configuration, the push rod 13 and striker plate 17 move to the left as shown in FIG. I until the reverse side of striker plate 17 seats on a seal surrounding the entrance to the port about bore 15 to seal off the intermediate chamber 14 from the first gas chamber 9. As pushrod 13 moves to the left so does push-rod 16 to release the bias on diaphragm 6 and thus allow a gas stream to pass through orifice 23. This situation is maintained until, for any reason, the supply of gas through the first gas supply line (and hence to first gas receiving means) fails or falls below the minimum predetermined safe operating pressure. Upon this eventuality arising spring 21 expands displacing diaphragm 11 to the right. Diaphragm 11 in turn displaces the pushrods 13 and 14 and diaphragm 12 to the right. This allows a portion of gas in the first gas conveying means to escape via the port about bore 15 into the intermediate chamber to activate the whistle. If (or as) the pressure of the first gas stream drops further striker plate 18 is displaced further to the right until it comes into contact with the operating rod of valve 20 and displaces the same to release the contents of the reserve gas tank 25 into the intermediate chamber 9. A portion of this gas flows out through the alarm whistle thus maintaining the audible warning while the remainder flows into the first gas chamber 9 via bore 15 and out through the inlet 2 of the first gas chamber into the first gas supply line to at least partially restore the first gas supply, this being possible since, when push-rod 13 is displaced to the right, striker plate 17 is out of contact with its associated valve seat thus placing intermediate chamber 19 in communication with first gas chamber 9. Once the supply of first gas is restored to the supply line a portion thereof may again pass through the inlet 2, into chamber 9 and through non-return valve 24 to recharge the reserve storage tank 25 until the pressure within the reservoir 25 is again restored to the predetermined value or desired supply pressure. The components are then restored to the normal operating position as depicted in the drawing and described above.

The various components are arranged in size and configuration to ensure that the force exerted by the first gas stream on the diaphragm 11 is greater than the force exerted by that portion of the same stream which escapes into the intermediate chamber on connection of the gas supply and acts on the striker plate 18. Thus the action which biases the diaphragm 11 to the left is greater than the tendency to maintain the striker plate 18 against the valve 20 to release gas from the interior of the reserve tank 25 into the intermediate chamber 19.

When used as a part of a gas anaesthetising plant a supply of oxygen is connected to the inlet 2 and a supply of nitrous oxide (N₂O) is provided to the inlet 4. Hence if there is a failure of the oxygen supply of any type, the supply of nitrous oxide will be automatically cut off. In the embodiment described, the tension of the spring 21 may be adjusted by means of screw 22 to suit individual requirements however the device is commonly set so that if the oxygen supply pressure falls below 40 psi the nitrous oxide supply will not flow and the alarm whistle activated. The non-return valve 24 is set so that oxygen will be stored in the reservoir 25 at a pressure of 55–60 psi which is the desired supply pressure of oxygen to a patient under anaesthetic. The whistle, upon a pressure of below 40 psi being sensed in the first gas stream, provides an audible warning of approximately 60 seconds duration. It will be appreciated that since the warning means 7, in the preferred form of this invention, is activated by gas from within the reserve storage means 25 the duration and intensity of the warning, i.e. the noise of the whistle, are independent of the rate at which the oxygen fails in the supply stream. As well as the warning given, an adequate supply of oxygen may be provided to the patient under anaesthetic for approximately 60 seconds. The above figures are obtained using a reserve storage means capacity of about 800 ml.

In a further aspect the invention provides a total anaesthetizing system comprising a primary source of life support gas for example oxygen; a source of anaesthetizing gas (for example nitrous oxide); a secondary source of life support gas; means to convey the gas from the sources to the patient; means through which the gases may be administered to the patient; and control means which in normal use, regulates or monitors only gas from the primary source of life support gas and from the source of anaesthetizing gas to the patient but which; on whole or partial failure of the primary source of life support gas, places the secondary source of life support gas in communication with the patient while stopping the supply of anaesthetizing gas to the patient.

The control means used together with the secondary source of life support gas is, in the preferred embodiment, the apparatus described above.

The major attributes of this device in its role in an anaesthetising system may be summarised briefly as follows:

It is operated entirely by the oxygen supply pressure and is fully automatic. There is no on/off switch. It is connected in the oxygen line before the flowmeter. When the oxygen supply is first activated, either by opening a cylinder or attaching pipeline gas, a short shrill sounding noise is made by the whistle until the quickly rising pressure exceeds 40 psi at which point the whistle will cease. This is an automatic test showing that the device is now ready to function in an emergency. When the pressure exceeds 40 psi, the nitrous oxide shut off valve is allowed to open and thus gas can then flow freely to the breathing circuit. The reserve cylinder (about 800 ml) is now pressurized to the normal working pressure (about 55 psi).

When the supply pressure falls below 40 psi, the warning whistle sounds, (indicating an emptying cylinder or broken or disconnected pipe line) and the nitrous oxide gas is immediately shut off and cannot be set flowing again until the oxygen supply pressure is re-established to above 40 psi. At this point the nitrous oxide flow will return automatically to its original setting. When the falling supply pressure reaches approximately 20 psi release valve 20 is activated releasing the stored oxygen in the reserve cylinder 25 (this reserve is kept at about 55 psi by virtue of a non-return valve in the inlet side and a release valve in the outlet side) into the intermediate chamber. The reserve cylinder has a dual purpose,—(1) It ensures the duration and intensity of the whistle are independent of the rate at which the oxygen fails and is sustained for approximately 60 seconds. (2) A portion of this reserve oxygen is channelled back through the flowmeter to the patient ensuring a continuing adequate supply average 400 ml/M flow for approximately 60 seconds.

It will thus be appreciated that the present invention provides a relatively simple yet effective means of meeting the stated object of the invention.

What is claimed is:

1. A warning and protection apparatus comprising:
   (a) a first gas supply line;
   (b) pressure responsive means communicable with said first gas supply line;
   (c) a second gas supply line;
   (d) first valve means disposed in said second gas supply line;
   (e) connection means connecting said pressure responsive means to said first valve means in a manner such that said first valve means closes upon said pressure responsive means experiencing a pressure below a predetermined level in said first gas supply line;
   (f) first gas reserve storage means;
   (g) second valve means actuable in the event of said pressure responsive means experiencing a pressure below said predetermined level to place said first gas reserve storage means in communication with said first gas supply line; and
   (h) audible gas operable alarm means communicable with said first gas supply line and said first gas reserve storage means upon said pressure responsive means experiencing pressure below said predetermined level.

2. Apparatus as claimed in claim 1 further comprising a first chamber connected to said first gas supply line, and wherein said pressure responsive means is disposed within said first chamber.

3. Apparatus as claimed in claim 2 wherein said pressure responsive means comprises a flexible diaphragm defining part of the wall of said first chamber and a biassing means to bias said diaphragm toward the interior of said first chamber.

4. Apparatus as claimed in claim 3 wherein said biassing means comprises a coil spring mounted to engage that side of said diaphragm remote from the interior of said fist chamber.

5. Apparatus as claimed in claim 4 wherein the compression of said spring is adjustable whereby the bias on said diaphragm may be adjusted to maintain the diaphragm in a substantially planar configuration when the pressure within said first chamber is at or above said predetermined level.

6. Apparatus as claimed in any one of claim 1 or 5 further comprising a second chamber in said second gas supply line having inlet and outlet connections and wherein said first valve means is located in said second chamber between said inlet and outlet connections.

7. Apparatus as claimed in claim 6 wherein the inlet to said second chamber includes an orifice and said first valve means comprises a second flexible diaphragm defining part of the wall of said second chamber, the axis of said orifice being substantially perpendicular to the plane of said second diaphragm, and said orifice being spaced from said diaphragm by a predetermined amount so that upon elastic deformation thereof said second diaphragm will contact and seal said orifice.

8. Apparatus as claimed in claim 7 wherein the diaphragm in said second chamber is mounted substantially parallel to the diaphragm in said first chamber.

9. Apparatus as claimed in claim 8 wherein said connection means is disposed between the two said diaphragms and adapted to function so that deflection of the diaphragm in said first chamber by the bias of said spring will result in deflection of the second diaphragm toward said orifice.

10. Apparatus as claimed in claim 9 wherein said connection means comprises a pair of coaxial pushrods.

11. Apparatus as claimed in claim 10 wherein at least one of said pushrods is provided with a striker plate.

12. Apparatus as claimed in claim 11 further comprising an intermediate chamber situated between said first and second chambers, said at least one striker plate is adapted for translational movement within said intermediate chamber and said intermediate chamber is communicable with said first chamber and said first gas reserve storage means when the pressure of gas within said first chamber is below said predetermined level.

13. Apparatus as claimed in claim 12 wherein said intermediate chamber is communicable with said first chamber through a port means concentric with and spaced around one of said pushrods leading from said intermediate gas chamber to the diaphragm in said first chamber and a valve seat is provided around the entrance of said port in said intermediate chamber so that the reserve side of the striker plate provided on that pushrod will seat on said valve seat and close said port when the gas within said first chamber is above said predetermined level.

14. Apparatus as claimed in claim 13 wherein said second valve means is actuable by a striker plate.

15. Apparatus as claimed in claim 12 wherein said audible alarm means comprises a gas operated whistle connected to said intermediate chamber.

16. Warning and protection apparatus comprising:
    means defining a body member;
    a first chamber within said body member, said first chamber being connectable to a first gas supply line;
    pressure responsive means within said first chamber;
    a second chamber within said body member, said second chamber having an inlet for connection to a second gas supply line and an outlet for connection to a second gas delivery line;
    first valve means within said second chamber for controlling the flow of gas between said inlet and outlet;
    connection means operatively disposed between said first valve means and said pressure responsive means;
    a reserve gas storage reservoir communicable with said first gas supply line; and
    an audible gas operable alarm means communicable with said first gas supply line and said reserve gas storage reservoir, the construction and arrangement being such that in use upon said pressure responsive means experiencing a pressure in said first chamber below a predetermined level, said first valve means is actuated to halt the flow of gas between said inlet and said outlet, said reserve gas storage reservoir is placed in communication with said first gas supply line and said audible alarm is placed in communication with said first gas supply line and said reserve gas storage reservoir.

* * * * *